United States Patent [19]

Goldenberg

[11] Patent Number: 5,101,827
[45] Date of Patent: Apr. 7, 1992

[54] LYMPHOGRAPHIC AND ORGAN IMAGING METHOD AND KIT

[75] Inventor: Milton D. Goldenberg, Short Hills, N.J.

[73] Assignee: Immunomedics, Inc., Warren, N.J.

[21] Appl. No.: 167,077

[22] Filed: Mar. 11, 1988

Related U.S. Application Data

[63] Continuation of Ser. No. 751,877, Jul. 5, 1985, Pat. No. 4,735,210.

[51] Int. Cl.⁵ ............................................. A61B 5/05
[52] U.S. Cl. ................................. 128/653.4; 424/9; 128/654
[58] Field of Search .................. 128/653, 654; 424/4, 424/9, 1.1; 436/806; 358/111; 324/309, 31

[56] References Cited

U.S. PATENT DOCUMENTS 4,643,884  9/1987  Kleiner et al. ........................... 424/9
4,647,447  3/1987  Gries et al. ............................... 424/9

OTHER PUBLICATIONS

R. O. Dillman et al., Blood, vol. 59, No. 5, May, 1982.
Textbook of Medical Physiology, Goyton, A., W. B. Saunders Co., Philadelphia, 1986, p. 361.
Goldenberg et al, Cancer Res. 36:3455-3463, Sep. 1976.
LeBien et al, J. Immunol., vol. 125, 2208, 1980.
Hsu et al., Am. J. Pathol., 114, 387-395 (1984).
Beverley et al., Eur. J. Immunol., vol. 11, 329 (1981).
Hsu et al., Am. J. Clin. Pathol., 80, 415-420 (1983).
Foon et al., Blood, 54(Suppl. 1):106a, 1979.
Royston et al., Blood, 60:1, 1982.

*Primary Examiner*—C. Fred Rosenbaum
*Assistant Examiner*—C. Maglione
*Attorney, Agent, or Firm*—Foley & Lardner

[57] ABSTRACT

An improved method for lymphoscintigraphy or magnetic resonance lymphography involves subtraction of a negative image produced using a gross imaging agent from a positive image produced with a specific antibody imaging agent. Another embodiment of the invention uses an antibody to lymphatic tissue as an imaging agent for lymphatics. A further embodiment uses a magnetic resonance image enhancing agent for magnetic resonance lymphography.

Reagents and kits for use in the foregoing method are also provided.

5 Claims, No Drawings

LYMPHOGRAPHIC AND ORGAN IMAGING METHOD AND KIT

This is a continuation of application Ser. No. 751,877 filed July 5, 1985 now U.S. Pat. No. 4,735,210.

BACKGROUND OF THE INVENTION

The present invention relates to a method for imaging lymphatic structures and to a kit suitable for use therefor.

There is a need, particularly in oncology, for a method that clearly delineates lymphatic structures. Lymphatic structures, particularly lymph nodes, drain tissue and extravascular regions of various molecular and macromolecular substances, including antigens, infectious agents, and cells, serving as a filter as well as a part of the host organism's immunological apparatus. It is well known that certain substances with appropriate physical properties, when injected into a suitable tissue plane, are transported from the injection site by a drainage system and sequestered in regional and then more distant lymph nodes. Some of these substances, particularly colloids, are passively retained in sinusoids and actively phagocytosed by the reticuloendothelial (RE) cells within the lymph node. When a radioisotope is incorporated in such a pharmaceutical suitable for lymphatic accretion, the lymph system, particularly the draining lymph nodes, can be imaged with a suitable scintigraphic system.

However, when a disease process impacts upon these lymphatic structures, the image of the lymph nodes may be affected in such a manner that their form and appearance is different. For example, a cancer infiltrating a lymph node may replace a large enough portion of the RE tissue in the node to exclude an imaging agent, e.g., a radiocolloid, from that area of the node, resulting in a "negative" image effect. Similar results may be obtained when the lymph node structure and function is compromised by infectious agents, e.g., bacteria, fungi, parasites and viruses.

However, the use of such lymphoscintigraphic methods can present problems in diagnostic interpretation, since "absent" lymph nodes or "decreased uptake of radioactivity" are not in themselves diagnostic of neoplastic or other involvement of the lymph nodes. Moreover, there may be lymph nodes that appear normal in the lymphoscintigram, or even show increased radiocolloid uptake, when these nodes are found to have metastases upon microscopic examination. Conversely, nodes with no apparent metastitic involvement may show decreased or no radiocolloid uptake. Thus, a method with greater specificity for lymph node involvement in cancer or in infectious diseases would be of considerable diagnostic value.

Methods of localization and therapy of tumors and infectious lesions using labeled antibodies and antibody fragments which specifically bind markers produced by or associated with tumors or infectious lesions have been disclosed, inter alia, in Hansen et al., U.S. Pat. No. 3,927,193 and Goldenberg, U.S. Pat. Nos. 4,331,647, 4,348,376, 4,361,544, 4,468,457, 4,444,744, 4,460,459 and 4,460,561, and in related pending applications U.S. Ser. Nos. 609,607 and 633,999, the disclosures of all of which are incorporated herein in their entireties by reference. See also Deland et al., *J. Nucl. Med.*, 20, 1243–50(1979).

These methods use radiolabeled antibodies which specifically bind to markers produced by or associated with tumors or infectious lesions, and result in a "positive" image, i.e., uptake of radioactivity attached to the antibody in the structure involved with tumor or infectious lesion and having the appropriate antibody target, thus permitting a visualization of the involved structure. Further improvements in the specificity and resolution of these methods is achieved by the use of various subtraction techniques which are also disclosed in the aforementioned references, and which enable background, non-specific radioactivity to be distinguished from specific uptake by the tumor or lesion.

Others have employed lymphoscintigraphy to study various types of cancers, using various imaging agents. Current lymphoscintigraphic methods employ Tc-99m antimony sulfide colloid (Tc-ASC) as the imaging agent of choice, although Tc-99m stannous phytate has also been reported as useful. See, e.g., Ege et al., *Brit. J. Radiol.*, 52, 124–9(1979); and Kaplan et al., *J. Nucl. Med.*, 20, 933–7(1979). Earlier, Au-198 colloid was used, as reported by, e.g., Hultborn et al., *Acta Radiol.*, 43, 52(1955); Turner-Warwick, *Brit. J. Surg.*, 46, 574(1959); Vendrell-Torne et al., *J. Nucl. Med.*, 13, 801(1972); Robinson et al., *Surg. Forum*, 28, 147(1977); Sherman et al., *Am. J. Roentgenol.*, 64, 75(1950); and Rosse et al., *Minerva Med.*, 57, 1151(1966). Intraperitoneal autologous Tc-99m-labeled erythrocytes were used in mediastinal lymphoscintigraphy to study ovarian cancer by Kaplan et al., *Br. J. Radiol.*, 54, 126(1981). Tc-99m-labeled liposomes were use in axillary lymphoscintigraphy of breast cancer by Osborne et al., *Int. J. Nucl. Med. Biol.*, 6, 75(1979). Tc-99m rhenium sulfide colloid was used in breast cancer lymphoscintigraphy by Gabelle et al., *Nouv. Presse Med.*, 10, 3067(1981). The use of Tc-ASC for lymphoscintigraphic imaging of mammary and prostatic cancers, as well as for malignant melanoma, has been reported by, e.g., Ege, *Sem. Nucl. Med.*, 13, 26(11983); Ege, *J. Urol.*, 127, 265–9 (1982); and Sullivan et al., *Am. J. Radiol.*, 137, 847–51(1981).

DeLand et al., *Cancer Res.*, 40, 2997–3001 (1980), disclose a scintigraphic imaging method using anti-carcinoembryonic antigen antibodies labeled with I-131. They found that the tumor marker, carcinoembryonic antigen (CEA), was accumulated in lymph node metastases and also in some non-metastatic lymph nodes in the drainage path of proximal tumors, and was revealed by binding to labeled antibody.

Lymph nodes have been imaged by magnetic resonance imaging techniques, but not with the use of image enhancing contrast agents, and not with antibody-conjugated imaging agents.

It is important in certain clinical situations to detect the presence or absence of a particular organ, such as the ovary. Moreover, it is often necessary to determine whether an organ is anatomically correct and whether it has pathology, e.g., obstruction, infection, neoplasia and the like, by a non-invasive technique. It would be desirable to have an organ imaging method using organ-specific imaging agents that would make it possible to obtain a "positive" image of the organ, when normal, and a defect in organ visualization if pathology is present. Such a method would provide a new approach to scintigraphic and magnetic resonance imaging of organs and tissues in the body based upon their immunological specificity.

Antibody conjugates comprising organ-specific and tissue-specific antibodies and addends for scintigraphic detection or magnetic resonance image enhancement have not been used as organ imaging reagents.

A need continues to exist for lymphographic imaging methods which are more sensitive and specific for tumor and infectious lesion involvement in lymphatic structures, and for organ imaging reagents and methods with high specificity for differentiation of particular organs and tissues from surrounding structures.

OBJECTS OF THE INVENTION

One object of the present invention is to provide a method for obtaining lymphoscintigraphic images that permits higher resolution and greater specificity for tumor or infectious lesion involvement with lymphatic structures.

Another object of this invention is to provide lymphomagnetic resonance imaging methods using image enhancing agents having organ-specific and/or tumor or lesion-specific properties as well as gross image enhancing agents.

Yet another object of the invention is to provide methods for lymphoscintigraphy and magnetic resonance lymphography which permit convenient subtraction of other organs such as the liver and spleen.

A further object of this invention is to provide organ-specific methods and agents for scintigraphic and magnetic resonance imaging.

Still another object of the invention is to provide a method of lymphographic imaging using a labeled antibody to an antigen produced by or associated with a tumor or lesion in the lymphatic structure or accreting in foci therein, wherein an early image is taken using the imaging agent as a gross imaging agent, after which specific uptake by antigen and clearance of non-specifically bound antibody is permitted to proceed, followed by taking a second image of the specifically bound agent, the former image being subtracted from the latter to enhance its image quality.

Yet a further object of the invention is to provide reagents and kits suitable for use in the lymphographic imaging methods of the invention.

Upon further study of the specification and appended claims, further objects and advantages of this invention will become apparent to those skilled in the art.

SUMMARY OF THE INVENTION

These objects can be achieved by providing a lymphographic imaging method for positive imaging of a tumor or infectious lesion or a localized product thereof in a mammalian lymphatic structure, comprising the steps of:

(a) parenterally injecting a mammalian subject, at a locus and by a route providing access to said lymphatic structure, with an amount of a gross lymphoscintigraphic imaging agent or lymphomagnetic resonance image enhancing agent sufficient to permit a scintigraphic image or an enhanced magnetic resonance image of said structure to be effected;

(b) obtaining a scintigraphic image or an enhanced magnetic resonance image of said structure, at a time after injection of said agent sufficient for said agent to accrete in said structure;

(c) simultaneously or at an earlier or later time, parenterally injecting said subject, at the same or different locus and by the same or different route, with an antibody or antibody fragment with specifically binds a maker produced by or associated with a tumor or infectious lesion, said antibody/fragment being labeled with a radioisotope capable of external detection or with a magnetic resonance image enhancing agent, the amount of the labeled antibody/fragment being sufficient to permit a scintigraphic image or an enhanced magnetic resonance image of the site or sites of specific uptake thereof to be obtained;

(d) obtaining a scintigraphic image or an enhanced magnetic resonance image of said site or sites, at a time after injection of said labeled antibody/fragment sufficient for said antibody/fragment to become specifically bound to said marker in said site or sites; and (e) subtracting the image obtained in step (b) from the image obtained in step (d), to produce a refined positive lymphographic image of said site or sites.

In another embodiment, the invention provides a lymphographic imaging method for positive imaging of a tumor or infectious lesion or a localized product thereof in a mammalian lymphatic structure, comprising the steps of:

(a) parenterally injecting a mammalian subject, at a locus and by a route providing access to said lymphatic structure, with an amount of a gross lymphoscintigraphic imaging agent or lymphomagnetic resonance image enhancing agent sufficient to permit a scintigraphic image or an enhanced magnetic resonance image of said structure to be effected; and (b) obtaining a scintigraphic image or an enhanced magnetic resonance image of said structure, at a time after injection of said agent sufficient for said agent to accrete in said structure;

wherein said gross imaging agent comprises an antibody/fragment which specifically binds to normal lymphatic cells or tissues, said antibody/fragment being labeled with a radioisotope or a magnetic resonance enhancing agent.

In yet another embodiment, the invention provides a lymphographic imaging method for positive imaging of a tumor or infectious lesion or a localized product thereof in a mammalian lymphatic structure comprising the steps of:

(a) parenterally injecting a mammalian subject, at a locus and by a route providing access to said lymphatic structure, with an amount of gross lymphomagnetic resonance imaging agent sufficient to permit an enhanced magnetic resonance image of said structure to be effected; and (b) obtaining an enhanced magnetic resonance image of said structure, at a time after injection of said imaging agent sufficient for said agent to accrete in said structure.

A further embodiment of the invention relates to scintigraphic and magnetic resonance organ imaging using antibodies that specifically bind to particular organs or tissues, and conjugated to radioisotopes and/or magnetic resonance image enhancing agents.

Still further improvements can be obtained by using antibodies to normal lymph node structures and/or tissues as the non-specific imaging agent and subtracting the resultant image from the positive image obtained using antibodies which specifically bind to tumors or infectious lesions.

Another embodiment of the invention relates to a method of lymphographic imaging wherein an early image is taken using a labeled specific antibody/fragment as a gross imaging agent, and a later image is taken after specific uptake by antigen and clearance of non-specifically bound antibody has occurred, the former image being subtracted from the latter to refine its image quality.

Reagents and kits useful for practicing the methods of the invention are also provided.

DETAILED DISCUSSION

In one methodological aspect, the present invention combines two approaches hitherto employed separately, in a way which has not been suggested in the earlier work on either technique. The work of DeLand, in collaboration with the present inventor, was related to localization of radiolabeled antibodies in tumors or accreted antigen foci of the lymphatics. The work of others was related to lymphoscintigraphic imaging of lymphatics with gross imaging agents. The present invention relates to the hitherto unsuggested correlation and computer processing of these two images to refine the positive image of a tumor or other pathological lesion, or accreted antigen focus, revealed by specific antigen-antibody binding.

The lymphographic method of the invention can be practiced either with scintigraphic or magnetic resonance imaging agents. A combination of these imaging agents can also be used, although this requires more complex instrumentation and data processing and may therefore be impractical in most cases. The subtraction of images can be readily achieved using conventional software. The imaging methods of DeLand et al., *Cancer Res.*, 40, 3046(1980), are illustrative of the computerized subtraction methods known in the art.

Major areas of interest for lymphography include regional spread of neoplastic and infectious lesions of the breast, colon and rectum, prostate, ovary and testes. Major lymph nodes involved in these various lesions include axillary and internal mammary nodes in the chest, and the pararectal, anterior pelvic (obturator), internal iliac (hypogastric), presacral, external and common iliac, and para-aortic nodes. Thus, applications where lymphographic imaging would be useful include, but are not limited to, pathological lesions affecting the major organs of the chest, abdomen and pelvis, as well as the skin, from which the regional and, subsequently, more distant lymphatics can be involved.

Scintigraphic imaging according to the method of the invention is effected by obtaining a scintigram of the lymphatic structure of interest, using as an imaging agent a radiolabeled antibody which specifically binds to a marker produced by or associated with a tumor or infectious lesion located in the structure or at a locus proximal to the structure and draining into the structure, such that the antigen/marker accretes in discrete foci therein; also obtaining a scintigram of the structure using a gross imaging agent which is a radiolabeled material which accretes in the structure but which does not specifically bind to the tumor or lesion, or to an accreted antibody focus; and subtracting the latter image from the former to produce a refined positive image of the site or sites of localization of the labeled specific antibody within the structure.

It will be appreciated that a specific labeled antibody/fragment imaging agent can function as a gross imaging agent for early imaging of a structure, when it is diffusely accreted therein, and still function at a later time as a specific imaging agent once clearance from organ background and localization/specific antigen-antibody binding at the site or sites of specific uptake by tumor, lesion or discrete antigen focus has occurred. This forms the basis for another embodiment of the present method.

The "gross" labeled imaging agent used to obtain the latter scinitgram may be a radiocolloid-type agent which is scavenged by the reticuloendothelial system (RES) and accretes in lymphatic structures. It may also be a radiolabeled liposome or a radiolabeled agent such as gallium citrate, labeled bleomycin, or the like, which accretes in lymphatics. Finally, and advantageously for certain cases, it may be a new type of gross imaging agent developed especially for this invention, namely, a radiolabeled antibody which specifically binds to normal lymphatic tissues or cells, but not to tumors or lesions located therein or proximal to and draining into the structure, so tat it is also diffusely distributed in the lymph nodes and reveals the internal structure thereof.

Examples of gross scintigraphic imaging agents include but are not limited to radiocolloids, e.g., Tc-ASC, Tc-99 sulfur colloid, Tc-99 stannous phytate, Au-198 colloid, Hg-197 sulfide colloid, In-111 phosphate colloid and the like, as well as the other types of agents reported in the literature, representative examples of which are disclosed hereinabove. Other colloidal preparations using radionuclides other than Tc or Au can be used, e.g., colloids In-111, Ru-97, Ga-67, and the like, or colloids incorporating I-131 or I-123. Such preparations are conventional and well known to the ordinary skilled artisan in this field. See, e.g., Rayudu, "Radiotracers for Medical Applications, Vol. I" (CRC Press, Boca Raton, Fla., 1983).

Radiolabeled antibodies to markers characteristic of lymphatic tissue are a new kind of gross imaging agent which are also useful in the method of the present invention. They are an example of an immunologic, organ-specific imaging agent which can be used to ascertain the location and shape of a specific organ and reveal possible abnormalities therein. Such agents are useful for imaging organs other than lymphatics, e.g., liver, spleen, pancreas, and the like, and many antibodies which specifically bind to tissues of these organs are known and/or under current investigation and development.

Organ-associated and organ-specific antibodies can be developed by immunizing a suitable animal host with certain mammalian tumors or normal organ/tissue extracts and/or cells. It is well known that use of tumors as immunogens can result in antibodies which not only react with neoplasia but also with normal tissue components which sometimes show an organ-restricted nature. Histogenetic and functional differences between various tissues and organs of the body of course suggest that distinct antigens are present and identifiable. A body of scientific literature already exists which claims the identification of organ-specific antigens, either using classical immunization approaches or by immunizing with specific tumors, and this is reviewed by Goldenberg et al., *Cancer Res.*, 36, 3455(1976), showing that such antigens are known and available.

Similar organ- and tissue-associated and specific antigens are identifiable by hybridoma methods which produce monoclonal antibodies. One recent development is the production of human hybridoma monoclonal antibodies by securing lymphocytes or plasma cells from patients showing certain organ-restricted autoimmune diseases, e.g., thyroiditis, gastritis, ulcerative colitis, myostitis, and the like. These antibody-producing cells are then fused in vitro with human or murine myeloma cells and hybridomas of appropriate anti-organ and anti-tissue antibody formation are produced and propagated, using well known methods. Also, patients with specific tumor types can be sued as a source of such lymphocytes or plasma cells, or such patients can be further immunized with such tumor cells for stimulating the production of anti-organ and anti-tissue antibodies. The lymphatic tissue removed is then used for fusion with suitable myeloma cells, by procedures which are by now well known and conventional in the art.

Organ-associated and organ-specific antigens can be isolated for immunization of another species, e.g., subhuman primates, rodents, rabbits, goats, etc., by a number of methods known in the art, such as isolation of cell membranes or disruption of the cells, e.g., by centrifugation, sonication, etc., to obtain intracellular antigens. It is preferable, for these purposes, to use intracellular as opposed to surface and extracellular antigens. In this manner, organ-associated and organ-specific antigens can be obtained from a large number of tissues and organs of the body, including brain, thyroid, parathyroid, larynx, salivary glands, esophagus, bronchus and lungs, heart, liver, pancreas, stomach and intestines, kidney, adrenal gland, ovary, testis, uterus, prostate, etc. Of further interest is the differentiation of different tissue and cellular components within an organ, such as tubular and glomerular kidney, different regions and cell types of the brain, endocrine and exocrine pancrease, etc., especially by the identification of antigens and antigen epitopes restricted to the individual cell and tissue types in question, as accomplished with polyclonal and/or hybridoma-monoclonal antibody-production methods known in the art.

Examples of antibodies which specifically bind to lymphatic cells and/or tissues, and which are useful as gross imaging agents when labeled with a radioisotope or magnetic resonance image enhancing agent, include the T101 murine monoclonal anti-T-cell antibody reported by Royston et al., *Blood*, 54(Suppl. 1), 106a(1979); and the T200 anti-lymphoreticular cell monoclonal antibody whose specificity was reported by Hsu et al., *Am. J. Pathol.*, 114, 387 (1984).Other antibodies to T-cells and B-cells, which can also be used for such agents, include, e.g., the B1, B2 and BA1 anti-B-cell monoclonal antibodies reported in Hsu et al., *Am. J. Clin. Pathol.*, 80, 415 (1983), and in Hsu et al., *Am. J. Pathol.*, 114, 387 (1984); the OKT10, A1G3, HLA-DR and Leu 10 monoclonals reported in Hsu et al., Ibid.; and anti-lymphocyte monoclonals reported by Foon et al., *Blood*, 60, 1 (1982), LeBien et al., *J. Immunol.*, 125, 2208(1980), and Beverley et al., *Eur. J. Immunol.*, 11, 329(1981).

The antibody may be whole IgG, IgA, IgD, IgE, IgM or a fragment such as, e.g, F(ab')2, F(ab)2, Fab', Fab or the like, including isotypes and subtypes thereof. It can be a polyclonal antibody, preferably an affinity-purified antibody from a human or an appropriate animal, e.g., a goat, rabbit, mouse or the like, or a monoclonal antibody prepared by conventional techniques, e.g., a murine antibody derived from a hybridoma produced by fusion of lymph or spleen cells from a mouse immunized against a lymphatic system antigen with myeloma cells from an appropriate immortal cell line.

It should be noted that mixtures of antibodies, isotypes, and immunoglobulin classes, including fragments, can be used, as can hybrid antibodies and/or antibody fragments. In particular, hybrids having both T101 and T200 specificities, or hybrids having anti-T-cell and anti-B-cell specificities, may be particularly useful as gross lymphatic imaging agents, both for scintigraphy and for magnetic resonance lymphography, depending upon the label or enhancing moiety conjugated thereto. Hybrid antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. Nos. 4,474,893 and 4,479,895, and in Milstein et al., *Immunol. Today*, 5, 299(1984).

The antibody/fragment used for the specific imaging agent can be any of the antibodies which bind to tumor-specific and/or tumor/associated markers such as those disclosed in the herein referenced U.S. Patents and Patent Applications, including hybrid antibodies and/or fragments, as well as others which are known to the ordinary skilled artisan in this field, e.g., antibodies which bind to human T-cell lymphoma viruses (HTLV), and those which are yet to be discovered. Also useful are antibodies to markers produced by or associated with infectious lesions of the lymphatic system, or lesions located proximal to and draining into lymph nodes. Lymphotropic microorganisms include bacteria. Viruses, parasites, and the like which show a predilection for sojourn in and involvement of lymphatic structures in the body. Among the viruses, the HTLV family have a predilection for T-lymphocytes, and are involved in leukemias, lymphomas, and AIDS. The HTLV form considered etiologic for AIDS is HTLV-III. Cytomegalovirus, EB herpes virus, and the like, also show some predilection for lymphatic structures although the site of primary infection can be other tissues, with subsequent involvement of lymphatic tissues. However, virtually all pathogenic microorganisms can demonstrate involvement of lymphatic tissues during passage and infection in the body.

Examples of antibodies to injections organisms and/or antigens produced by or accreted by or in the vicinity of infectious lesions include, e.g., antibodies against variola virus, yellow fever virus, arboviruses, herpes viruses, myxoviruses, enteroviruses, rabies virus, hepatitis A and B viruses, Chlamydia psittaci, Rickettsia prowazeki and other rickettsia, lymphocytic choriomeningitis virus, Neisseria meningitidis, Neisseria gonorrhoeae, Corynebacterium diphtheriae, Clostridium tetani, Bacillus anthracis, Yersinia pestis, Vibrio cholerae, salmonella and shigella bacterial species, staphylococci species, Reponema pallidum, leptospiral species, Mycobacterium leprae, Mycobacterium tuberculosis, Histoplasma capsulatum, Coccidioides immitis, various streptococci, Plasmodium falciparum and other plasmodia, Toxoplasma gondii, Leishmania donovani, various trypanosomes, Entameba histolytica, Giardia lambia, Trichinella spiralis, Strongyloides stercoralis, Antiostrongylus cantonensis, Wucheria bancrofti, Schistosoma mansoni and other schistosomal helminths, Paragonimus westermani, echinococcal species, and the like. Listings of representative disease-causing infectious organisms to which antibodies can be developed for use in this invention are contained in the second and subsequent editions of Davis et al, "Microbiology" (Harper & Row, New York, 1973 and later), and are well known to the ordinary skilled art worker.

Again, the antibody may be whole IgG, IgA, IgD, IgE, IgM or a fragment such as, e.g., F(ab')2, F(ab)2, Fab', Fab or the like, including isotypes and subtypes thereof. It can be a polyclonal or a monoclonal antibody/fragment, a mixture of antibodies/fragments or a hybrid. Here, where the image is produced as a result of specific antibody-antigen binding rather than non-specific uptake by the RES, it may be especially advantageous to use antibody fragments which do not have the Fc portion.

The radiolabel for both types of scintigraphic imaging agents is preferably an isotope with an energy in the range of 50-500 Kev. Where more than one isotope is used for simultaneous subtraction, the two labels should be of sufficiently different energies to be separately detectable with a gamma camera having a collimator with the appropriate characteristics.

Many of the preferred radiocolloids are available commercially or can be prepared according to conventional methods reported in the literature, including the illustrative references hereinabove. Colloids having a particular range of particle size are optimal for interstitial administration and subsequent uptake by the lymphatic system draining into lymph nodes of interest. A particle size of less than 25 nm, e.g., 0.1-25 nm, preferably 1-20 nm, is preferred for optimal mobilization. Control of the particle size as a function of the gelling conditions for the colloid is conventional in the art and can be done without undue experimentation by the skilled artisan.

Commercial colloids are available with acceptable particle sizes, e.g., 198-Au colloid with a particle size of 2-10 nm, 99m-Tc sulphide colloid with a high but nevertheless usable particle size over 100 nm, and 197-Hg sulphide colloid with a particle size of 10-150 nm. 99m-Tc stannous phytate is ionic, and 51-Cr and 99m-Tc human serum albumin are proteinaceous with mw 60,000.

The alternative type of gross imaging agent disclosed hereinabove, i.e., an antibody to a marker associated with lymphatic tissue, can be prepared by known methods, if existing antibodies are considered unsuitable or if different or more discriminating specificities are desired. Generally, whole lymph cells, tissue samples and/or cell or tissue fractions, membranes, antigen extracts or purified surface antigens are used to challenge the immune system of a suitable animal, e.g., a mouse, rabbit, hamster, goat or the like, the antigen being rendered immunogenic by aggregation if necessary and/or by coadministration with a suitable conventional adjuvant. Hyperimmune antiserum can be isolated and polyclonal antibodies prepared by conventional procedures. Alternatively, spleen cells can be fused with immortal myeloma cells to form hybridoma cells producing monoclonal antibodies, by what are now conventional procedures. See, e.g., the procedures in the above-referenced U.S. patent application Ser. No. 609,607 for illustrative techniques. Hybridomas using animal, e.g., mouse, or human myeloma cell lines and animal or human spleen or lymph cells are all known in the art, and can be made and used for the present method. See, for example, Glassy et al., "Human Monoclonal Antibodies to Human Cancers", in "Monoclonal Antibodies and Cancer", Boss et al., Eds., 163-170 (Academic Press, 1983). The specific antisera or monoclonals are screened for specificity by methods used to screen the anti-lymphocyte clones in the references cited hereinabove, which methods are also conventional by now in this art.

In an alternative embodiment of this approach, the gross agent can be a labeled antibody to a marker associated with a lymphatic structure, e.g., lymphatic tissues or lymphocytes, wherein the antibody also specifically binds to a marker produced by or associated with liver and/or spleen tissues or components. Among the anti-lymphatic clones disclosed hereinabove, at least the anti-T101 antibody is also cross-reactive with spleen. Antibodies which are cross-reactive with both lymphatic tissue/cells and liver and/or spleen cells/tissue can also be prepared by well-known hybrid antibody production techniques, such as those disclosed in the above-referenced U.S. Pat. Nos. 4,331,647, 4,474,893 and 4,479,895. These would combine anti-lymph tissue antibodies with antibodies which specifically bind to liver and/or spleen.

Such antibodies can be produced using liver cells isolated from normal liver tissue obtained at autopsy. For example, mice can be immunized with such tissues for a period necessary to evoke anti-liver antibodies. The spleens of these mice are removed and then fused, by standard methods, with a murine myeloma cell line suitable for hybridoma production. Using methods already standard in the art, monoclonal antibody-producing hybridomas are selected and propagated, and those with liver-restricted or liver-associated antibody production are cloned and expanded as a source of liver organ antibodies.

Similar approaches can be used with human tumors or other normal human tissues for the production of antibodies that are organ-associated or tissue-specific. Absolute tissue specificity is not required since significant quantitative differences ordinarily suffice for operational specificity for imaging purposes.

It will also be appreciated that the anti-liver antibodies can be used as a liver background subtraction agent when visualizing tumors in the liver. These tumors can be of non-liver origin or of liver origin. Even if a tumor of liver origin has the liver organ-associated antigen, subtraction of the latter can be accomplished without missing the tumor if another liver cancer-associated antigen is used as the target for the specific anti-liver cancer antibody. For example, antibody against alpha-fetoprotein (AFP) can be used in combination with an antibody against normal liver organ antigen, thus refining the image of areas containing AFP in the liver.

The antibodies can be radiolabeled by a variety of methods known in the art. Many of these methods are disclosed in the above-referenced U.S. Patents and Patent Applications, and include direct radioiodination, chelate conjugation, direct metallation, and the like. See also, Rayudu, op. cit.; and Childs et al., *J. Nuc. Med.*, 26, 293(1985). Any conventional method of radiolabeling which is suitable for labeling isotopes for in vivo use will be generally suitable for labeling imaging agents according to the present invention.

The gross imaging agent will normally be administered at a site and by means that insure that it is mobilized and taken up into the lymphatic circulation. This will vary with the system to be imaged. Multiple injection sites may be preferable in order to permit proper drainage to the regional lymph nodes under investigation. In some cases, injections around the circumference of a tumor or biopsy site is desired. In other cases, injection into a particular sheath or fossa is preferred. Injection into the webs of the fingers or toes is a common mode used to study peripheral lymphatics.

For example, for visualization of the internal mammary lymphatics in breast cancer with Tc-ASC, the radiocolloid is injected into the posterior rectus sheath at the insertion of the diaphragm in the subcostal site, using about 0.5 mCi of radiocolloid in a volume usually not exceeding about 0.3 ml. This method can also be used to visualize iliopelvic lymphatics in genitourinary cancers. In patients with breast carcinoma, a unilateral injection is made in the subcostal site ipsilateral to the tumor, and then repeated later on the contralateral side to observe cross drainage between the ipsilateral and contralateral nodes. Imaging is effected at appropriate times after each injection and injection of the specific imaging agent is coordinated with the injections of the gross imaging agent to permit optimal visualization of the positive and negative images.

Images of axillary, subclavian and supraclavicular nodes may be obtained by injecting the imaging reagents into the medial surface of the upper arms (ipsilateral and contralateral) of patients with breast cancer.

Another approach is to inject about 0.1–0.5 mCi of Tc-ASC around the areola tissue of the breasts bilaterally, and the image the axilla. In addition to periareolar injection, interdigital administration of radiocolloid may be used for visualization of axillary lymphatics (see, DeLand et al., 1980, loc. cit.). Combined interdigital and periareolar administration of radiocolloid can provide increased accuracy to demonstrate decreased uptake in affected axillary nodes. Intratumoral injection of, e.g., Tc-99m rhenium colloid has been performed in patients with breast cancer and is a useful mode of administration for certain cases.

For lymphoscintigraphy of genitourinary cancers or lesions, bilateral deep perianal injection of radiocolloid and specific imaging agent into the ischiorectal fossa is effective. For example, the patient can be placed in the lithotomy position and about 1 mCi of Tc-ASC in a volume less than about 0.3 ml is introduced bilaterally into the ischiorectal fossa, e.g., with a 22 gauge needle, to a depth of about 1.5 inches just lateral to the anal margin, at the 9 and 3 o'clock positions. The patient may also lie on the side is achieving the lithotomy position is not possible. Subcutaneous dorsal pedal injection of about 1 mCi of Tc-ASC and/or specific imaging agent may be made, e.g., using a 27 gauge half-inch needle in the first interdigital spaces bilaterally.

In certain cases, such as testicular or prostatic cancer or some cases of rectal carcinoma, intratumoral or peritumoral injection of imaging agents can be effective.

The cross-reactive agent is preferably injected by a systemic route, e.g., intravenously, intraarterially, intramuscularly or subcutaneously, or by a combination of systemic and intralymphatic routes insuring its accretion in both the lymphatic structure of interest and the liver and/or spleen. This technique permits subtraction of the liver and/or spleen which can further refine the image of the desired lymphatic structure. Another advantage of this approach is its utility in reducing repositioning errors in sequential imaging wherein a patient is imaged in multiple sessions. The organ image can be used to correlate and superimpose temporally discrete images by computer matching of the organ image from the separate sessions.

Volumes of colloid preparations are normally about 0.1–2.0 ml, preferably about 0.2–1.0 ml, per injection site, but this can vary depending on the site and the number of injections. Volumes of labeled antibody gross imaging agent, normally in sterile phosphate-buffered saline (PBS) solution or sterile mineral oil suspension, will normally vary somewhat depending upon the site, the concentration and activity of the preparation, and the number of injections.

Activity of the gross agent will normally be in the range of about 0.1–2.5, preferably about 0.25–1.5, mCi per injection for a Tc-99m-labeled agent. Using Tc-ASC, doses of 0.25–1.0 mCi per injection are given for normal injections. It will be appreciated that the activity will vary for other radioisotopes, depending upon their half-lives, their imaging characteristics, i.e., energy ranges, emission intensities, scatter and the like, the stability of the labeled agent, especially antibody conjugates, their rate of transport to the lymph nodes, their distribution and clearance, and the time at which imaging is to be done. Adjustment of these parameters will be conventional for the ordinary skilled clinician.

Imaging is normally effected up to about 6 hours, more preferably at about 2–4 hours after injection of the gross imaging agent, to obtain the "negative" image of the lymphatic structure. Imaging of the localized specific imaging agent is normally effected at about 12–48 hours, preferably at least about 24 hrs post-injection, in order for the non-specifically bound antibody to clear the node. If too much of the specific agent enters the circulation, conventional subtraction agents, e.g., 99m-pertechnetate and Tc-99m-HSA can be used to normalize. Alternatively, second antibody, e.g., rabbit or goat anti-mouse IgG, can be injected i.v. to enhance clearance of the specific antibody, as disclosed in U.S. Ser. No. 633,999.

Timing of the injections of gross and specific imaging agents will depend upon the types of agents used and the drainage patterns to the nodes of interest. Normally, it will taken the specific agent a longer time to localize, and for the non-localized agent to clear the nodes, than the time required before imaging can be effected with the gross imaging agent. Thus, if it is desired to image both agents at about the same time, the specific imaging agent may need to be injected well before the gross agent. DeLand et al., 1980, loc. cit., reported imaging at between about 6 and 48 hours post-injection for breast cancer cases, where I-131-labeled anti-CEA antibody was injected in the webs of the fingers and feet. Combination of this procedure, according to the invention, with interdigital injection of Tc-ASC is advantageously effected by injection of the colloid about 20–36 hours after injection of the labeled antibody, and imaging of the axillary, subclavian and supraclavicular nodes about 2 hours later, using a collimator which permits separate acquisition of the I-131 and Tc-99m radiation.

It is generally preferred to effect imaging of both the gross and specific agents at the same time, using separately detectable radionuclides. This avoids the errors associated with repositioning the patient and/or realigning the images by computer. Consequently, the choice of label for the gross and specific imaging agents and the activities thereof will take into consideration the time intervals for imaging. The specific antibody imaging agent normally will have a label with at least as long a half-life as the gross agent. In the earlier example hereinabove, the antibody is labeled with I-131, and the gross agent has a Tc-99m label. The antibody could be labeled with In-111 and the gross agent with Ga-67, both of which have about the same half-life of about 2.5 days. Other pairs of compatible radionuclides for use in labeling the specific and gross imaging agents are disclosed in, e.g., the above-referenced U.S. Pat. No. 4,444,744.

In another alternative embodiment of the invention, a labeled specific antibody is administered by a route and mode which ensures accretion in a lymph node to be imaged, an early image is taken when the major portion of the antibody is grossly accreted in the lymph node, e.g., after 3-6 hours, and a later image is taken after the major portion of non-localized antibody has cleared and the major portion, e.g., at least 50%, preferably at least about 70%, and more preferably at least about 90%, of the labeled antibody/fragment remaining in the lymph node has been specifically bound by antigen at discrete sites in the structure. The earlier image is then subtracted by computer processing from the later image to generate a refined position image of the structure.

The scintigram is normally taken by a gamma imaging camera having one or more windows for detection of energies in the 50-500 keV range. Use of radioisotopes with high enough energy beta or positron emissions would entail use of imaging cameras with the appropriate detectors, all of which are conventional in the art.

The scintigraphic data are stored in a computer for later processing. Subtraction of the "negative" image obtained with the gross imaging agent sharpens and refines the "positive" image obtained with the specific, localized labeled antibody. Subtraction is effected by the method of DeLand et al., op. cit., or variants thereof, according to well-known techniques of data processing, normally involving pixel-by-pixel subtraction of normalized values of counts for each channel of the detector, optionally with correction for the counting efficiency of each channel for the radionuclide label detected therein, and conversion of the subtracted values to an output signal to a monochrome or color screen. Where cross-reactive antibodies are used as the gross imaging agent, computer subtraction of the image of the cross-reactive organ is also effected to further resolve the positive image of the localized antibody site or sites.

If no tumor or lesion is present in the structure, but marker accretes there by drainage from a proximal tumor or infection, the marker can accrete in discrete foci within the lymph nodes in the drainage path. This can be visualized using the present method, since the gross imaging agent will still enable subtraction of areas of only diffuse accretion. The diagnostic significant of such foci of antigen accretion may be difficult to evaluate, and to distinguish from small metastases, but this problem is common to earlier methods and must be resolved by correlation of imaging data with other diagnostic results. It will be recognized that use of only gross imaging agents fails to reveal such antigen localization, i.e., foci of antigen accretion, which often suggest eventual invasion of tumor cells and also reveal tumor drainage pathways.

Another important application of the organ- or tissue-specific or organ- or tissue-associated antibodies disclosed hereinabove is for normal organ scintigraphy and mri. In this case, a suitably radiolabeled antibody/fragment or an antibody/fragment bearing a mr image enhancing agent is administered with the intention of obtaining a "positive" image of the organ, when normal, and a defect in organ visualization if pathology is present. This provides a new approach to organ and tissue-specific nuclear and magnetic resonance imaging of organs and tissues in the body, based upon their immunological specificity.

It will be understood that the invention is not limited to use of known antibodies or markers, but can be practiced with antibodies to any marker produced by or associated with a tumor or other pathological lesion.

Magnetic resonance imaging (mri) is effected in an analogous manner to scintigraphic imaging except that the imaging agents will contain magnetic resonance (mr) enhancing species rather than radioisotopes It will be appreciated that the magnetic resonance phenomenon operates on a different principle from scintigraphy. Normally, the signal generated is correlated with the relaxation times of the magnetic moments of protons in the nuclei of the hydrogen atoms of water molecules in the region to be imaged. The magnetic resonance image enhancing agent acts by increasing the rate of relaxation, thereby increasing the contrast between water molecules in the region where the imaging agent accretes and water molecules elsewhere in the body. However, the effect of the agent is to decrease both $T_1$ and $T_2$, the former resulting in greater contrast while the latter results in lesser contrast. Accordingly, the phenomenon is concentration-dependent, and there is normally an optimum concentration of a paramagnetic species for maximum efficacy. This optimal concentration will vary with the particular agent used, the locus of imaging, the mode of imaging, i.e., spin-echo, saturation-recovery, inversion-recovery and/or various other strongly $T_1$-dependent or $T_2$-dependent imaging techniques, and the composition of the medium in which the agent is dissolved or suspended. these factors, and their relative importance are known in the art. See, e.g., Pykett, *Scientific American*, 246, 78(1982); Runge et al., *Am. J. Radiol.*, 141, 1209(1983).

Again, the gross agent can be a colloid or a labeled antibody to a normal component of lymphatic structures, labeled with a paramagnetic ion or radical which can significantly alter the relaxation time of protons in water molecules in its vicinity. It is also possible to use an agent containing a high concentration of atoms of an element other than hydrogen, having a strong nuclear magnetic moment which is detectable by an nmr detector, e.g., Fluorine-19 and the like, and which can also be accreted in a lymphatic structure in an amount sufficient for efficient nmr detection.

Examples of RE colloids useful for mri of lymphatic systems include Gd(III), Eu(III), Dy(III), Pr(III), Pa(IV), Mn(II), Cr(III), Co(III), Fe(III), Cu(II), Ni(II), Ti(III) and V(IV) colloids, colloids of other strongly paramagnetic ions, or radicals, e.g., nitroxides, and antibody conjugates bearing paramagnetic ion chelates or radical addends. The latter will include paramagnetic conjugates with antibodies to lymphatic structures or lymphocytes, for use as gross imaging agents, as well as conjugates with antibodies to tumor or lesion markers for use as specific imaging agents.

The specific imaging agent can use the same image enhancing agent, with mri effected at different times from the gross imaging, or a label which is separately and independently detectable with an nmr imaging camera, in the presence of the agent used for gross imaging. Examples of the latter strategy include, e.g., use of antibody conjugates with heavy loadings of Gd(III) or Mn(II) chelates as the specific imaging agent, where the gross imaging agent is a colloid containing a high concentration of fluorine atoms or atoms of another suitable element having a strong nuclear magnetic moment, whose nuclear magnetic resonance frequency occurs at a widely different value from that of the hydrogen nucleus.

The mr image enhancing agent must be present in sufficient amounts to enable detection by an external camera, using magnetic field strengths which are reasonably attainable and compatible with patient safety and instrumental design. The requirements for such agents are well known in the art for those agents which have their effect upon water molecules in the medium, and are disclosed, inter alia, in Pykett, op. cit., and Runge et al., op. cit.

Preparation of antibodies conjugated to a magnetic resonance image enhancing agent can be effected by a variety of methods. In order to load an antibody molecule with a large number of paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbones, polyoximes, and the like groups known to be useful for this purpose. The chelate is normally linked to the antibody by a group which enables formation of a bond to the antibody with minimal loss of immunoreactivity and minimal aggregation and/or internal cross-linking. Other, more unusual, methods and reagents for conjugating chelates to antibodies are disclosed in copending U.S. patent application Ser. No. 742,436 to Hawthorne, entitled "Antibody Conjugates", filed June 7, 1985, the disclosure of which is incorporated herein in its entirety by reference.

The mr scans are stored in a computer and the image subtraction is effected analogously to the scintigraphic data.

Reagents for use in the method of the invention include radiocolloids, radiolabeled antibodies/fragments which specifically bind to markers produced by or associated with tumors and infectious lesions, radiolabeled antibodies/fragments which specifically bind to lymphatic structural components, including tissues and lymphocytes, radiolabeled antibodies/fragments which specifically bind to normal organ tissues, and the analogous imaging agents labeled with mr image enhancers, as disclosed hereinabove. These will be packaged separately or together, depending upon whether they are to be injected simultaneously or separately, or whether or not they are labeled at the site of administration or at a remote location.

The reagents are conveniently provided in kit form, adapted for use in the method of the invention. Kits will normally contain separate sealed sterile vials of injectable solutions of labeled reagents, or lyophilized antibodies/fragments or antibody/fragment conjugates and vials of suitable conventional injection vehicles with which they will be mixed just prior to administration.

Kits may also include reagents for labeling antibodies, e.g., Chloramine-T (for I-131 or I-123 labeling), $SnCl_2$ (for Tc-99m labeling using pertechnetate from a commercial generator), short columns for sizing and/or purification of reagents, and other conventional accessory materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Preparation of lymphoscintigraphic reagents a) Ga-67-labeled T101 anti-lymphocyte monoclonal antibody A sample of T101 anti-lymphocyte murine monoclonal antibody, as reported by Royston et al., loc. cit., is labeled with Ga-67 by the method of Hnatowich et al., *Science*, 220, 613(1983), to form the conjugate with a diethylenetriaminepentaacetate (DTPA) gallium(III) chelate, containing an average of 4 Ga atoms per antibody molecule, and retaining at least 70% of its initial immunoreactivity. A solution of the antibody in PBS, pH 7.4, is added to a 50-fold molar excess of solid DTPA dianhydride, and agitated for 5 minutes. Free DTPA is removed by gel filtration on Sephadex G 50. About 1 mCi Ga-67 citrate is added per mg of antibody-DTPA conjugate, and incubated for 20 minutes, and unbound Ga-67 is then removed, e.g., by gel filtration on Sephadex G 50. The resultant Ga-67-DTPA-T101 has a specific activity of about 0.5–1.5 mCi/mg.

b) I-131-labeled T101 anti-lymphocyte monoclonal antibody

A sample of the T101 monoclonal antibody used in Example 1 is labeled with I-131 according to the procedure of Example 1(f) of U.S. Pat. No. 4,348,376, using Chloramine-T and replacing the anti-CEA antibody used in the referenced procedure with an equal weight of T101 antibody, but reducing the amounts of reagents to lower the iodine content. The resultant I-131-T101 has an average of 1 atom of iodine per antibody molecule and a specific activity of about 12 mCi/mg.

c) In-111-labeled anti-HTLV-1 monoclonal antibody

A sample of murine monoclonal anti-HTLV-1 antibody is labeled with In-111 according to the procedure of part (a) hereof, except that In-111 oxinate is used instead of Ga-67 citrate, to form the conjugate with a DTPA indium(III) chelate, containing an average of 3 In atoms per antibody molecule, and retaining at least 70% of its initial immunoreactivity. The resultant In-111-DTPA-anti-HTLV-1 has a specific activity of about 0.5–1.5 mCi/mg.

d) In-111-labeled anti-prostatic acid phosphatase F(ab')$_2$

A sample of anti-prostatic acid phosphatase (PAP),-F(ab')$_2$, prepared by the method disclosed in U.S. Pat. No. 4,331,647, and described in Goldenberg et al., *J. Am. Med Assn.*, 250, 630(1983), is labeled with In-111, using the procedure of part (c) hereof. The resultant In-111-DTPA-chelate conjugate contains an average of 3 In atoms per antibody fragment, and retains at least 60% of its initial immunoreactivity. It has a specific activity of about 2 mCi/mg.

e) I-123-labeled anti-CEA monoclonal antibody

A sample of the NP-2 monoclonal antibody which specifically binds to carcinoembryonic antigen (CEA), disclosed in U.S. Ser. No. 609,607 is labeled with I-123 according to the procedure of Example 1(f) of U.S. Pat. No. 4,348,376, using Chloramine-T and replacing the I-131 used in the referenced procedure with an equal weight of I-123, but reducing the amounts of reagents to lower the iodine content. The resultant I-123-anti-CEA IgG has an average of 1 atom of iodine per antibody molecule and a specific activity of about 12 mCi/mg.

EXAMPLE 2

Preparation of injectable lymphoscintigraphy compositions

Sterile, pyrogen-free solutions are prepared as shown.
a) a sterile solution containing, per ml:
  1) 10 mg Human Serum Albumin (HSA) (1%, USP, Parke-Davis)
  2) 0.01M phosphate buffer, pH 7.5 (Bioware)
  3) 0.9% NaCl
  4) 1.5 mg Ga-67-DTPA-T101 antibody prepared according to Example 1a.
b) A sterile solution according to Example 2a, except that 250 ug of the I-131-labeled antibody according to Example 1b is present instead of the Ga-labeled antibody.
c) A sterile solution according to Example 2a, except that 1.5 mg of the In-111-labeled antibody according to Example 1c is present instead of the Ga-labeled antibody.
d) A sterile solution according to Example 2a, except that 1.5 mg of the In-111-labeled antibody according to Example 1d is present instead of the Ga-labeled antibody.
e) A sterile solution according to Example 2a, except that 250 ug of the I-123-labeled antibody according to Example 1e is present instead of the Ga-labeled antibody.

EXAMPLE 3

Preparation of Reagents for NMR Lymphography a) Preparation of Gd-labeled anti-CEA A sample of murine monoclonal antibody to carcinoembryonic antigen (CEA), prepared according to Example 2 of U.S. Pat. No. 4,348,376 or according to Examples 6 and 7 of U.S. Ser. No. 609,607, is labeled with a p-isothiocyanatobenzoyl-capped aligothiourea containing 320 Gd(III)- DTPA chelate groups prepared according to Example 11 of copending U.S. Ser. No. 742,436, to put an average of 5 oligothiourea chains on the antibody, without loss of more than 30% immunoreactivity and without significant aggregation of the antibody conjugate. The resultant conjugate carries an average of 320 gadolinium ions thereon. The reaction is effected in 0.1M aqueous $Na_2CO_3/NaHCO_3$ buffer, at pH 8.5, at room temperature, with at least a 50-fold excess of the polymer, and an antibody concentration of about 10 mg/ml.

The conjugate is purified by gel filtration on a column of allyl dextran cross-linked with N,N'-methylene bisacrylamide, e.g., Sephacryl S-200 (Pharmacia Fine Chemicals, Piscatoway, N.J.).

b) Preparation of Gd(III)-labeled T101 monoclonal antibody.

A sample of T101 murine monoclonal antibody is labeled with about 320 Gd ions by the procedure of part (a) hereof, except that the antibody is the T101 antibody instead of monoclonal anti-CEA IgG. The resultant conjugate is isolated by an analogous procedure to the foregoing part of this Example.

c) Preparation of Cu(II) sulfide colloid

CuS sulfur colloid is prepared by bubbling $H_2S$ into an acidified solution of $CuCl_2$, in the presence of oxygen and gelatin, and isolating the resultant colloid.

EXAMPLE 4

Preparation of injectable mri compositions

Sterile, pyrogen-free solutions are prepared as shown.
a) A sterile solution containing, per ml:
  1) 10 mg Human Serum Albumin (HSA) (1%, USP, Park-Davis)
  2) 0.01M phosphate buffer, pH 7.5 (Bioware)
  3) 0.9% NaCl
  4) 1.5 mg Gd-labeled anti-CEA IgG prepared according to Example 3a.
b) A sterile solution according to Example 4a, except that 1.5 mg of the Gd-labeled T101 according to Example 4b is present instead of the Gd-labeled anti-CEA.

EXAMPLE 5

Lymphoscintigraphy

A male with proven prostatic carvinoma is being evaluated for ileopelvic lymph node spread. He is positioned supine on the pelvic examination table in the lithotomy position. Two injections (approximately 2 mCi each) of Tc-99m-ASC(as supplied by Cadema Medical, Inc., Westtown, N.Y. 10998) and of 111-In-labeled F(ab')$_2$ against prostatic acid phosphatiase (PAP) prepared according to Example 2(d) herein, are made just lateral to the anal margin, at 3 and 9 o'clock. The needle is held parallel to the tabletop and is inserted to its full length of 1½ inches (22-gauge) into the ischiorectal fossa. Within each injection is contained 1 mCi each of the 99m-Tc and the 111-In preparation, which are mixed in the syringe for simultaneous application. (It may be preferred to first inject the antibody fragment and then, 1-2 hrs. later, the antimony sulfide colloid.)

About 3 hrs after the injections, the patient is imaged with a medium-resolution collimator, collecting about 100,000 to 200,000 counts per view, followed by repeated imaging at 8 and 24 hours. Images are taken in the anterior, posterior, and lateral projections. The images made by the two isotopes with different energies are then computer-subtracted according to the method described by DeLand et al., *Cancer Res.*, 40, 3046(1980), whereby the lymph-node image of the Tc-99m-ASC is subtracted, pixel-by-pixel, from that of the In-111-labeled anti-PAP antibody fragment. At 3 hrs after injection of the preparations, and again at 8 hrs., the right obturator and internal iliac nodes are visualized as having abnormal radioactivity following perianal injection. Images of the 99m-Tc colloid alone or of the 111-In-antibody alone were equivocal for lymph node involvement, indicating the superiority of the combined (double isotope and agent) approach.

EXAMPLE 6

Lymphoscintigraphy

A patient with carcinoma of her right breast receives injections of approximately 0.25 mCi 131-I-labeled T101 monoclonal antibody according to Example 2(b), subcutaneously in the web of the fingers of both hands (totalling 0.7 to 1.5 mCi 131-I). The patient also receives, in the same injections, 1.5 mCi 123-I-labeled monoclonal anti-CEA antibody NP-2, according to Example 2(e), (totalling 4.2 to 9.0 mCi 123-I). Before administration of the labeled antibodies, the patient is skin-tested for allergic reaction to mouse IgG, and also receives Lugol's iodine to minimize radioiodine concentration by the thyroid gland. Immediately following the subcutaneous injection, the areas are massaged for several minutes, and the patient is asked to exercise her fingers.

By means of a gamma camera, images are obtained at frequency intervals, starting at 2 hrs. after injection and ending at 36 hrs. The data are stored in a laboratory computer and the images generated on a color display system. The 131-I images are then subtracted, pixel-by-pixel, from the 123-I images by computer processing. The metastatic foci in the ipsilateral axillary lymph node appear as early as 4 hrs., and more clearly at 6 hrs., after injection as a discrete focus of increased radioactivity, while the contralateral axillary nodes are negative. Two weeks later, the same procedure is repeated and the results confirmed, except that this time, 111-In is used to label the T101 monoclonal antibody.

Another study with 99m-Tc sulfide colloid injected simultaneously with 111-In-labeled anti-CEA monoclonal antibody, effected as above but with the appropriate doses for these radionuclide and agents, is repeated a month later and the right axillary lymph node involvement is seen again.

EXAMPLE 7

Lymphoscintigraphy

A 24 year old male presents with left side inguinal node enlargement and has a constellation of symptoms and history suggestive of Aids. 67-Ga-labeled T101 monoclonal antibody, according to Example 2(a), is injected in divided doses into the web of the toes of both feet, with a total dose of 4 mCi. At the same time and in the same injections, an equal dose of 111-In-labeled monoclonal antibody against HTLV-1, according to Example 2(c), is injected. Beginning at 2 hrs post-injection and continuing at intervals of 2 hrs up to a total of 6 hrs, and then again at 24 hrs., the patient's inguinal region and pelvis is imaged with a medium-energy collimator and using the subtraction method described above to subtract the 67-Ga images from the 111-In images. At 4 hrs, and the improving by 6 hrs., a positive image of the left inguinal node is noted while the right inguinal node is virtually negative.

EXAMPLE 8

Organ Scintigraphy

Hybridoma-monoclonal antibodies are made in the mouse to the Langerhans cells of the endocrine pancreas, derived from a human autopsy specimen shortly after death. The monoclonals reactive against the antigen epitopes showing relatively high specificity for Langerhans cells of the pancreas, as demonstrated, e.g., by immunohistology, are labeled with a gamma-emitting isotope, such as with I-131, and injected, e.g., 0.15 mg monoclonal against endocrine pancrease antigen, labeled using Chloramine-T with I-131, at a dose of 1.0 mCi, injected i.v. in a 3month old male suspected of having pathology of the endocrine pancreas. External gamma-camera imaging is performed at 24, 48, 72, and 96 hours after injection without subtraction. In this specific case, decreased to almost absent accretion of I-131 radioactivity in the pancrease is suggestive of endocrine pancrease pathology in an infant presenting with pancreas hormone deficiency shortly after birth.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A lymphographic imaging method for imaging of a tumor or infectious lesion or a localized product thereof in a mammalian lymphatic structure, comprising the steps of:
   (a) parenterally injecting a mammalian subject, at a locus and by a route providing access to said lymphatic structure, with an amount of a gross lymphoscintigraphic imaging agent or lymphomagnetic resonance image enhancing agent sufficient to permit a scintigraphic image or an enhanced magnetic resonance image of said structure to be effected; and
   (b) obtaining a gross scintigraphic image or a gross enhanced magnetic resonance image of said structure, at a time after injection of said agent sufficient for said agent to diffusely accrete in said structure;
   wherein said gross imaging agent comprises an antibody or antibody fragment which specifically binds to normal lymphatic cells or tissues, said antibody or antibody fragment being labeled with a radioisotope or a magnetic resonance image enhancing agent.

2. The method of claim 1, wherein said gross antibody or antibody fragment is labeled with a magnetic resonance image enhancing agent.

3. The method of claim 1, wherein said antibody or antibody fragment is labeled with a radioisotope.

4. A method of organ imaging in a mammalian subject by scintigraphy or magnetic resonance imaging, comprising the steps of:
   (a) patenterally injecting a mammalian subject, at a locus and by a route providing access to an organ of interest, with an antibody or antibody fragment which specifically binds a marker produced by or associated with said organ, said antibody or antibody fragment being labeled with a radioisotope capable of external detection or with a magnetic resonance image enhancing agent, the amount of the labeled antibody or antibody fragment being sufficient to permit a scintigraphic image or an enhanced magnetic resonance image of said organ to be obtained; and
   (b) obtaining a positive scintigraphic image or a positive enhanced magnetic resonance image of said organ, at a time after injection of said agent sufficient for said agent to diffusely accrete in said organ and specifically bind to said marker.

5. The method of claim 4, wherein said marker is an intracellular marker.

* * * * *

UNITED STATES PATENT AND TRADEMARK OFFICE
CERTIFICATE OF CORRECTION

PATENT NO. : 5,101,827        Page 1 of 2

DATED : April 7, 1992

INVENTOR(S) : Milton D. Goldenberg

It is certified that error appears in the above-identified patent and that said Letters Patent is hereby corrected as shown below:

Column 2, line 29; "use" should read --used--;

Column 3, line 68, "maker" should read --marker--;

Column 6, line 17, "tat" should read --that--;

line 27, "colloids" should read --colloidal--;

Column 8, line 26, "bacteria. Viruses," should read --bacteria, viruses,--;

line 39, "injections" should read --infectious--;

Column 13, line 47, "significant" should read --significance--;

Column 14, line 30, "these" should read --These--;

Column 16, line 56, "(PAP),-- should read --(PAP--;

Column 19, line 20, "frequency" should read --frequent--;

line 34, "radionuclide" should read --radionuclides--.

UNITED STATES PATENT AND TRADEMARK OFFICE
CERTIFICATE OF CORRECTION

PATENT NO. : 5,101,827

DATED : April 7, 1992

INVENTOR(S) : Milton D. Goldenberg

It is certified that error appears in the above-indentified patent and that said Letters Patent is hereby corrected as shown below:

Column 20, Claim 2, line 1, delete "gross".

Signed and Sealed this

Thirty-first Day of May, 1994

Attest:

BRUCE LEHMAN

Attesting Officer     Commissioner of Patents and Trademarks